(12) United States Patent
Sharma et al.

(10) Patent No.: US 6,506,456 B1
(45) Date of Patent: Jan. 14, 2003

(54) METHOD FOR APPLICATION OF A FLUID ON A SUBSTRATE FORMED AS A FILM OR WEB

(75) Inventors: Varunesh Sharma, Atlanta, GA (US); Robert John Schwartz, Cumming, GA (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 115 days.

(21) Appl. No.: 09/672,736

(22) Filed: Sep. 28, 2000

Related U.S. Application Data

(60) Provisional application No. 60/162,531, filed on Oct. 29, 1999.

(51) Int. Cl.[7] .................................................. B05D 1/04
(52) U.S. Cl. ..................... 427/466; 427/469; 427/482; 427/483; 427/485; 347/112
(58) Field of Search ......................... 427/466, 467, 427/469, 475, 482, 483, 485; 347/112

(56) References Cited

U.S. PATENT DOCUMENTS

| | | | |
|---|---|---|---|
| 3,338,992 A | | 8/1967 | Kinney |
| 3,341,394 A | | 9/1967 | Kinney |
| 3,502,763 A | | 3/1970 | Hartmann |
| 3,542,615 A | | 11/1970 | Dobo et al. |
| 3,692,618 A | | 9/1972 | Dorschner et al. |
| 3,802,817 A | | 4/1974 | Matsuki et al. |
| 3,849,241 A | | 11/1974 | Butin et al. |
| 4,340,563 A | | 7/1982 | Appel et al. |
| 4,345,907 A | * | 8/1982 | Wegele et al. |
| 5,057,368 A | | 10/1991 | Largman et al. |
| 5,069,970 A | | 12/1991 | Largman et al. |
| 5,110,618 A | * | 5/1992 | Faust |
| 5,149,563 A | | 9/1992 | Collier |
| 5,277,976 A | | 1/1994 | Hogle et al. |
| 5,466,410 A | | 11/1995 | Hills |
| 5,683,752 A | * | 11/1997 | Popp et al. |
| 5,827,255 A | | 10/1998 | Crainic |

FOREIGN PATENT DOCUMENTS

| | | | |
|---|---|---|---|
| DE | 35 39 781 | | 5/1987 |
| DE | 196 36 234 | | 3/1998 |
| DE | 197 53 602 | | 6/1999 |
| EP | 362 602 | | 4/1990 |
| EP | 437 383 | | 7/1991 |
| EP | 600 454 | | 6/1994 |
| GB | 956564 | | 4/1964 |
| WO | 96/00548 | | 1/1996 |
| WO | 96/00549 | | 1/1996 |
| WO | 97/02903 | * | 1/1997 |

* cited by examiner

*Primary Examiner*—Fred J. Parker
(74) *Attorney, Agent, or Firm*—Pauley Petersen Kinne & Eirckson

(57) ABSTRACT

A method for application of a fluid on a substrate formed as a film or web or laminate in which the substrate is located between two spaced apart electrodes for generating an electrostatic field. An electrostatic field is generated on each side of substrate and a fluid is introduced as droplets for application to the substrate into the electrostatic field on at least one side of the substrate, forming electrostatically charged droplets. The electrostatically charged droplets are directed based upon a predetermined pattern onto the at least one side of the substrate. In accordance with one embodiment, the electrode on the side opposite to the side on which the droplets are introduced is used to cause the droplets to migrate into the interior of the substrate.

10 Claims, 2 Drawing Sheets

METHOD FOR APPLICATION OF A FLUID ON A SUBSTRATE FORMED AS A FILM OR WEB

BACKGROUND OF THE INVENTION

This application claims the benefit of Provisional Application No. 60/162,531, filed Nov. 29, 1999.

FIELD OF THE INVENTION

This invention relates to a method for application of a fluid to films and web materials which provides high speed multi-dimensional discrete registered placement of chemistry to enhance chemical functionality, appearance and structural integrity. The result of this method is material and consumer products with anisotropic chemical and physical properties in three dimensions. This method is particularly suitable for producing materials comprising gradients of such properties along any of the three dimensions. The method of this invention is particularly advantageous when used in connection with materials used in the production of personal care articles such as diapers, incontinence garments, training pants, feminine hygiene products such as sanitary pads and panty liners, and medical garments such as surgical gowns as it enables the deposition of chemical treatments at locations in the articles most beneficial to the use of the article. For example, in a diaper, it may be more beneficial to concentrate a chemical treatment for enhancement of fluid distribution only at the primary point of insult rather than have the chemical treatment located in places in which it may not be necessary.

GENERAL BACKGROUND

Current methods for applying chemical treatments to substrate materials such as films and material webs often involve little control over the placement of the chemical treatments on or within the substrate materials. These methods include coating, spraying and dipping which do not permit placement of chemicals on such substrates with three-dimensional control over concentration of chemicals in substrates. Traditional spray technologies are relatively inefficient in placement of chemicals on the substrates, each droplet cannot be individually controlled for discrete placement, and only the directly exposed parts of the substrate are covered. U.S. Pat. No. 5,869,172 teaches a process for treating a porous substrate such as a fabric to produce internally coated porous materials in which a curable thixotropic material and one or more modifying materials are applied to the porous substrate as an impregnant. Sufficient energy is directed to the impregnant and porous substrate to cause the impregnant to flow into the porous substrate and force the modifier to specific positions within the substrate.

Printing techniques for application of inks to films and material webs are known; however, these techniques are typically limited to placement of the inks only on the surfaces of such substrates and do not permit placement of chemicals within the interior of the substrates, much less with three-dimensional control over chemical concentrations within the substrate. Such printing techniques include inkjet printers which employ computer controlled electrostatic charges for deposit of inks with a high degree of accuracy. See, however, International Publication No. WO 98/09798 which teaches a three dimensional printing materials system and method of use which includes building cross-sectional portions of a three-dimensional article and assembling the individual cross-sectional areas in a layerwise fashion to form a final article. The individual cross-sectional areas are built by using an ink-jet printhead to deliver an aqueous solvent to an adhesive particulate mixture, causing the particles of the mixture to adhere together and to the previous cross-sectional areas.

Various webs and films have been electrically charged to enhance one or more properties of the web or film being treated. This includes the electrostatic treatment of various webs and films to enhance properties such as wettability, printability, adhesion and static reduction among others. Generally speaking, such treatments are achieved by directing a web or film which is to be electrically charged between a coupled pair of conducting bodies. One of the conducting bodies, if desired, may serve to direct the web or film through the charging apparatus. The other conducting body operates to develop a potential difference such that ionization and corona occurs. In this way, an electrostatic discharge is created between the conducting bodies, through which the web can pass to receive the desired treatment. U.S. Pat. No. 5,766,425 teaches a method for modifying the surface of a substrate to be treated in which an electrode structure causes an electric field/current to pass generally horizontally across the surface of the electrode structure and the substrate to be treated is positioned adjacent to the surface of the electrode structure, in turn, causing the discharge to flow horizontally across the substrate, thereby modifying the surface of the substrate so as to achieve an improvement in the desired properties.

Other methods employing electrostatic systems for applying materials to a substrate are taught, for example, by U.S. Pat. No. 4,748,043 in which an electrostatic coating system for applying a very thin coating to a substrate in air at atmospheric pressure comprises a plurality of spaced capillary needles disposed concentrically within the holes of an extractor plate, positioned in at least two rows and fed with coating liquid through a manifold, and a potential is developed between the capillary needles and the extractor plate affording a reduction of the liquid to a mist of highly charged droplets drawn to the substrate by a second electrical field; by related U.S. Pat. No. 5,552,012 and 5,585,170 which teach a method of using an electric field for contacting a substantially neutrally charged material, that is responsive to an electric field, with a substrate; and U.S. Pat. No. 5,807,437 which teaches a three-dimensional printing technique using a layered process in which a continuous-jet inkjet printer is used to deliver a binder to a bed of porous materials.

U.S. Pat. No. 4,859,266 teaches a method and apparatus for powder sewing two plies of cloth or fabric material by spraying an adhesive powder onto one side of one ply of cloth or fabric from a powder spray gun having a corona discharge electrode mounted thereon. A second pin electrode is provided on the opposite side of the one ply of cloth or fabric. Electrical charges of differing polarity are applied to the electrodes while the cloth or fabric is moved between them and the powder is sprayed thereon. In the course of migrating through the electrostatic field created between the two electrodes, the powder is caused to follow the force lines created within that field and to migrate onto one side of fabric in the form of a long, narrow band of powder. A second ply of cloth or fabric is placed over the first ply and the band of powder at which point pressure and heat are applied, activating the powder and causing it to become tacky, where, upon cooling, the two plies adhere together.

In contrast to known methods whereby powder (solid) materials can be made to migrate from one side of a porous substrate to the opposite side by application of an electrostatic field on both sides of the substrate material, the chemical treatments of interest in personal care absorbent articles are frequently fluids (liquids). It will be apparent to those skilled in the art that control of fluid distribution within a porous substrate is substantially different from the control of powder distribution within a porous substrate as taught by the prior art due to the differences in the physical properties of solids and liquids.

SUMMARY OF THE INVENTION

It is one object of this invention to provide a method for producing a material such as a fabric, textile, nonwoven or film having a gradient of at least one desired physical/chemical property, which gradient may extend in any one of an X, Y, or Z-direction of the material. As used herein, the X-direction and the Y-direction correspond to the directions of two perpendicular lines disposed in the same plane, and the Z-direction corresponds to the direction of a line perpendicular to the plane of the X- and Y-directions.

It is another object of this invention to provide a method for placement of fluids on and within substrates by which placement of each droplet of fluid can be individually controlled.

It is yet another object of this invention to provide materials suitable for use in personal care absorbent articles having chemical gradients extending in at least one of an X, Y and Z-direction.

It is yet another object of this invention to provide a method for placement of fluids on and within substrates which produces greater accuracy than conventional technologies.

It is a further object of this invention to provide a method for placement of fluids on and within substrates which is generally faster, more efficient and more reliable than conventional technologies.

These and other objects of this invention are addressed by a method for application of a fluid on a substrate formed as a film or web comprising the steps of locating the substrate between two spaced apart means for generating an electrostatic field, generating an electrostatic field on each side of the substrate, introducing a fluid as droplets for application to the substrate into the electrostatic field on at least one side of the substrate, thereby forming electrostatically charged droplets, and directing the electrostatically charged droplets based upon a predetermined pattern onto the at least one side of the substrate. The direction of the electrostatically charged droplets is preferably controlled by a computer generated signal. By appropriate control of the electrostatically charged droplets, the fluid may be caused to migrate from one side of the substrate into an interior portion of the substrate, i.e in the Z-direction. Similarly, the fluid may also be caused to migrate in the X- and Y-directions. In addition, by controlling the migration of the fluid within the substrate, fluid density gradients within the material may be generated.

BRIEF DESCRIPTION OF THE DRAWINGS

These and other objects of this invention will be better understood from the following detailed description taken in conjunction with the drawings wherein.

DESCRIPTION OF PREFERRED EMBODIMENTS

Definitions

Figure 1:
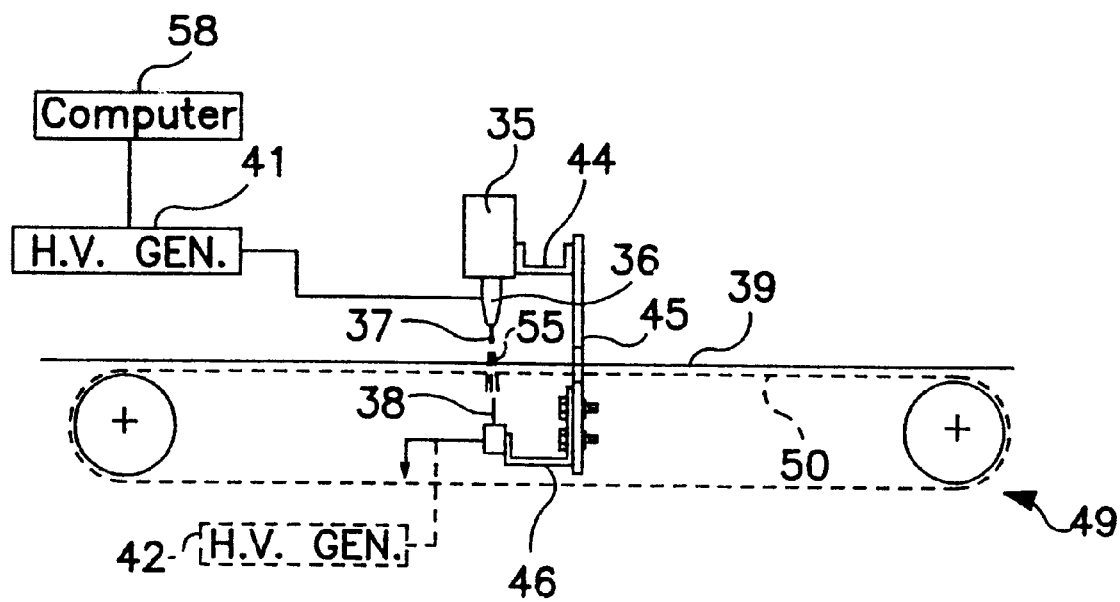
FIG. 1 is a schematic diagram of a lateral view of a system for application of fluids to a porous substrate in accordance with one embodiment of the method of this invention.

As used herein, the term "comprising" is inclusive or open-ended and does not exclude additional unrecited elements, compositional components, or method steps.

As used herein, the term "nonwoven web" means a web that has a structure of individual fibers or threads which are interlaid, but not in an identifiable repeating manner. Nonwoven webs have been, in the past, formed by a variety of processes such as, for example, meltblowing processes, spunbonding processes, coforming processes, hydroentangling, air-laid and bonded carded web processes.

As used herein, the term "spunbond fibers" refers to small diameter fibers which are formed by extruding molten thermoplastic material as filaments from a plurality of fine, usually circular capillaries of a spinneret, with the diameter of the extruded filaments then being rapidly reduced as by, for example, in U.S. Pat. No. 4,340,563 to Appel et al., U.S. Pat. No. 3,692,618 to Dorschner et al., U.S. Pat. No. 3,802,817 to Matsuki et al., U.S. Pat. No. 3,338,992 and 3,341,394 to Kinney, U.S. Pat. No. 3,502,763 to Hartmann, and U.S. Pat. No. 3,542,615 to Dobo et al. Spunbond fibers are generally not tacky when they are deposited onto a collecting surface. Spunbond fibers are generally continuous and have average diameters (from a sample of at least 10 fibers) larger than 7 microns, more particularly, between about 10 and 30 microns. The fibers may also have shapes such as those described in U.S. Pat. No. 5,277,976 to Hogle et al., U.S. Pat. No. 5,466,410 to Hills, and U.S. Pat. Nos. 5,069,970 and 5,057,368 to Larginan et al., which describe hybrids with unconventional shapes. A nonwoven web of spunbond fibers produced by melt spinning is referred to as a "spunbond".

As used herein, the term "meltblown fibers" means fibers formed by extruding a molten thermoplastic material through a plurality of fine, usually circular, die capillaries as molten threads or filaments into converging high velocity, usually hot, gas (for example, air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed, for example, by U.S. Pat. No. 3,849,241 to Butin et al. Meltblown fibers are microfibers which may be continuous or discontinuous, and are generally smaller than 10 microns in average diameter.

As used herein, the term "bonded carded web" refers to webs made from staple fibers which are sent through a combing or carding unit, which breaks apart and aligns the staple fibers in the machine direction to form a generally machine direction-oriented fibrous nonwoven web. Such fibers are usually purchased in bales which are placed in a picker or fiberizer which separates the fibers prior to the carding unit. Once the web is formed, it is then bonded by one or more of several known bonding methods.

As used herein, the term "polymer" generally includes, but is not limited to, homopolymers, copolymers, such as for example, block, graft, random and alternating copolymers, terpolymers, etc., and blends and modifications thereof. In addition, unless otherwise specifically limited, the term "polymer" also includes all possible geometric configurations of the molecule. These configurations include, but are not limited to, isotactic, atactic, syndiotactic and random symmetries.

As used herein, the term "microfibers" refers to small diameter fibers having an average diameter not greater than about 75 microns, for example, having an average diameter of from about 0.5 microns to about 50 microns, or more particularly, having an average diameter of from about 2 microns to about 40 microns. Another frequently used expression of fiber diameter is denier, which is defined as grams per 9000 meters of a fiber, and may be calculated as fiber diameter in microns squared, multiplied by the density in grams/cc, multiplied by 0.00707. A lower denier indicates a finer fiber and a higher denier indicates a thicker or heavier fiber. For example, a diameter of a polypropylene fiber given as 15 microns may be converted to denier by squaring, multiplying the results by 0.89 g/cc and multiplying by 0.00707. Thus, a 15 micron polypropylene fiber has a denier of about 1.42. Outside the United States, the unit of measurement is more commonly the "tex", which is defined as the grams per kilometer of fiber. Tex may be calculated as denier/9.

As used herein, the term "personal care absorbent article" means disposable diapers, training pants, absorbent underpants, adult incontinence products, feminine hygiene products including sanitary pads and napkins, wipes, tissues, bandages, dressings and the like.

The invention disclosed herein is a method for applying fluids to substrate materials formed as webs and films, including, nonwovens, textiles, fabrics, and the like whereby a fluid suitable for providing desired chemical treatments or finishes so as to provide the materials with anisotropic properties is deposited on and within the substrate materials. Chemical treatments and finishes applied in accordance with the method of this invention are in the form of fluids (liquids) which enhance or provide a desired functionality to the substrate material, such as hydrophilic, hydrophobic, anti-static, stain-blocking, and stain-resistance properties, to name a few. Suitable chemical treatments for achievement of these functional properties are known to those skilled in the art. Such treatments and finishes may also be used to enhance the structural integrity of the substrate materials or enhance aesthetics such as by applying dyes and pigments. These chemical treatments and finishes are applied, in accordance with the method of this invention, in a registered manner, that is, in a manner by which precise control is maintained over the placement of the materials in accordance with a predetermined pattern or arrangement.

The method of this invention employs continuous or drop-on-demand ink-jet technology, which technology allows for the discrete placement of electrostatically chargeable droplets of fluids on the desired substrate. This discrete placement of fluid drops is accomplished by means of a computer generated signal from a computer operably connected to the fluid placement device, such as an ink-jet printer. Current ink-jet technology is capable of generating droplets at rates up to 200 kHz, which translates into a capability of generating $1 \times 10^6$ drops/second. This technology is capable of high printing speeds providing the potential for treatment of substrates moving at a linear speed of 800 inches/second and placement of fluid resulting in a resolution of 1250 drops/inch. However, current ink-jet technology does not provide any means for penetration of the substrate by the deposited materials and, thus, is limited to surface applications.

In accordance with the method of this invention, an electrostatic charge, which is also computer controlled, is applied to the side of the substrate material opposite the side on which the ink-jet printer is disposed by any means suitable for generation of an electrostatic charge. Thus, as the substrate material passes between the two electrostatic fields, a fluid is introduced in the form of droplets into the electrostatic field generated, for example, by the ink-jet printer or an external source, resulting in electrostatically charged droplets. The electrostatically charged droplets are directed in a predetermined pattern onto the substrate material. This predetermined pattern may include material density gradients disposed on the surface of the substrate material. The electrostatic field disposed on the side of the substrate material opposite the side on which the electrically charged droplets are disposed is applied to the substrate material, also in accordance with a predetermined pattern which is also computer controlled, as a result of which the electrostatically charged droplets are caused to migrate into the interior of the substrate material. The extent of the droplet migration into the interior of the substrate material may be controlled by altering the strength and/or the location of the electrostatic field. In addition, by varying the potential intensity of the electrostatic field in a pattern, materials having varying Z-direction concentrations may be produced. Thus, by judicious control of the electrostatic field, the placement of the electrostatically charged droplets to generate a gradient in the X-, Y-, and/or Z-direction within the substrate material is possible, resulting in substrate materials having anisotropic properties. Thus, for example, anisotropic fluid distribution within the substrate material is possible.

Suitable substrate materials include, but are not limited to, wovens, films and nonwovens, including spunbond, meltblown and bonded carded webs, and laminates and composites thereof. These substrates may be three-dimensional fibrous webs comprising fibers of a range of linear and bulk densities. The substrate materials treated in accordance with the method of this invention may be used in personal care articles, resulting in personal care articles having anisotropic properties.

In accordance with one embodiment of this invention, the fluid distributed on and/or within the substrate material is an adhesive. By virtue of the computer controlled signal, the adhesive may be applied at pre-determined locations, thereby enabling the achievement of any of a number of unique substrate properties, which are not currently possible with conventional spray technologies which have no means for providing fluid penetration into and through the substrate material.

Referring to FIG. 1, there is shown in diagrammatic form one portion of an apparatus for producing anisotropic substrate materials in accordance with the method of this invention. The apparatus comprises a liquid spray reservoir 35 having a nozzle 36 attached thereto. A liquid droplet charging electrode 37 extends from the nozzle 36. A second electrode or counter electrode 38 is mounted beneath the substrate material 39 to which the liquid is applied. A high voltage generator 41 connected to electrode 37 supplies high voltage power to that electrode. A high voltage generator 42 is connected to the counter electrode 38 for providing a high voltage of opposite polarity. The liquid spray reservoir 35 is mounted on a supporting arm 44, which connects it to a holding frame 45. Similarly, counter electrode 38 is mounted on support 46, which, in turn, is attached to the holding frame 45. A conveyor belt 49 passes between the electrode 37 and the counter electrode 38. The conveyor belt is an electrically non-conductive net or mesh type belt 50 upon which the substrate material 39 is supported and moved thereby between the electrode 37 and the counter electrode 38. In one embodiment of this invention, the substrate is a continuous substrate moving on the conveyor belt 49 between the electrode 37 and the counter electrode 38 at a linear speed of at least about 400 inches/second. The net or mesh type belt 50 is operative to transmit electrostatic force lines 55 between the electrode 37 and the counter electrode 38. A computer 58, operatively connected to the high voltage sources, controls the voltage applied to each of the electrode and the counter electrode.

Figure 2:
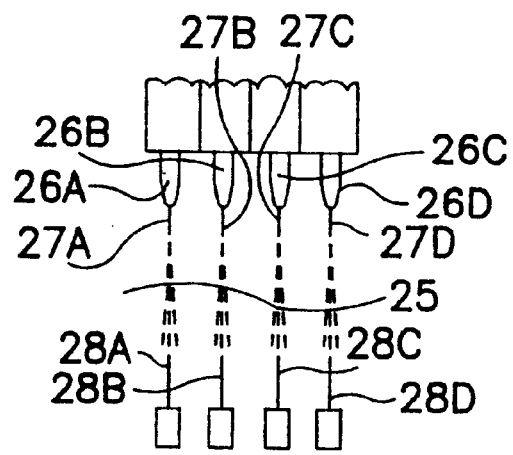
FIG. 2 is a partially schematic side view of a modification of an apparatus for use in the practice of this invention.

FIG. 2 shows a second form of an apparatus suitable for use in the practice of this invention. In this embodiment, multiple nozzles 26A, 26B, 26c, 26D are provided, from each of which extends an electrode 27A–27D. Counter electrodes 28A–28D are located on the underside of substrate material 39. Each of the electrodes and counter electrodes is capable of independent operation based upon a computer generated signal.

Figure 3:
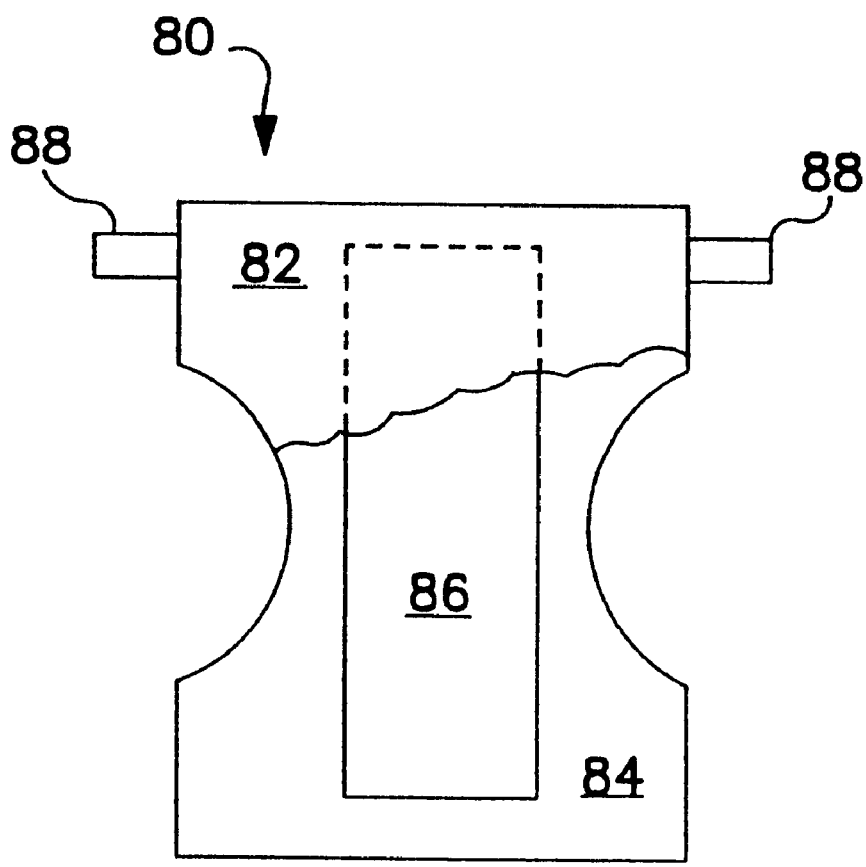
FIG. 3 is a partially cut away top plan view of an exemplary personal care absorbent article, in this case a diaper, which utilizes a nonwoven treated in accordance with the method of this invention.

As has been stated previously, the treated substrate materials of this invention may be used in a wide variety of applications, not the least of which includes personal care absorbent articles such as diapers, training pants, incontinence devices and feminine hygiene products such as sanitary napkins. An exemplary article 80, in this case a diaper, is shown in FIG. 3 of the drawings. Referring to FIG. 3, most such personal care absorbent articles 80 include a liquid permeable top sheet or liner 82, a back sheet or outer cover 84 and an absorbent core 86 disposed between and contained by the top sheet 82 and back sheet 84. Articles 80 such as diapers may also include some type of fastening means 88 such as adhesive fastening tapes or mechanical hook and loop type of fasteners.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

We claim:

1. A method for application of a fluid on a substrate formed as a film or web or laminate comprising the steps of locating said substrate between two spaced apart means for generating an electrostatic field;

generating an electrostatic field on each side of said substrate;

introducing, on at least one side of said substrate, a fluid as droplets for application to said substrate into said electrostatic field, forming electrostatically charged droplets;

directing said electrostatically charged droplets based upon a predetermined pattern onto said at least one side of said substrate, the directing controlled by a computer generated signal; and causing said electrostatically charged droplets to migrate from said one side of said substrate into an interior portion of said substrate by the computer controlled electrostatic field on the other side of said substrate, resulting in chemically generated anisotropy through the thickness of the substrate.

2. A method in accordance with claim 1, wherein said migration of said fluid results in generation of a. fluid gradient within said substrate.

3. A method in accordance with claim 1, wherein said substrate is a nonwoven material.

4. A method in accordance with claim 3, wherein said nonwoven material comprises a material selected from the group consisting of spunbond, meltblown, bonded carded web and combinations thereof.

5. A method in accordance with claim 1, wherein said fluid comprises a substrate treatment agent selected from the group consisting of hydrophilic, hydrophobic, anti-static, stain-blocking, stain-resisting and combinations thereof.

6. A method in accordance with claim 1, wherein said fluid comprises a coloring agent selected from the group consisting of dyes and pigments.

7. A method in accordance with claim 1, wherein said substrate is a continuous material moving at a linear speed between said means for generating said electrostatic field of at least about 400 inches/second.

8. A method in accordance with claim 7, wherein said directing of said electrostatically charged droplets produces a resolution of at least about 200 drops/inch.

9. A method in accordance with claim 1, wherein said substrate is a 3-dimensional fibrous web.

10. A method in accordance with claim 1, wherein said fluid is an adhesive.

\* \* \* \* \*